s008491633B2

(12) United States Patent
Pasquet et al.

(10) Patent No.: US 8,491,633 B2
(45) Date of Patent: Jul. 23, 2013

(54) INTERVERTEBRAL SPACER FOR CERVICAL VERTEBRAE

(75) Inventors: Denis Pasquet, Quinsac (FR); Régis Le Couedic, Andresy (FR)

(73) Assignee: Zimmer Spine, Bordeaux (FR)

( * ) Notice: Subject to any disclaimer, the term of this patent is extended or adjusted under 35 U.S.C. 154(b) by 1051 days.

(21) Appl. No.: 11/596,519

(22) PCT Filed: May 13, 2005

(86) PCT No.: PCT/FR2005/001202
§ 371 (c)(1),
(2), (4) Date: Nov. 14, 2006

(87) PCT Pub. No.: WO2005/122924
PCT Pub. Date: Dec. 29, 2005

(65) Prior Publication Data
US 2008/0033557 A1 Feb. 7, 2008

(30) Foreign Application Priority Data

May 17, 2004 (FR) .................................... 04 05333

(51) Int. Cl.
*A61B 17/70* (2006.01)
*A61F 2/44* (2006.01)

(52) U.S. Cl.
USPC ...... 606/246; 606/249; 623/17.11; 623/17.16

(58) Field of Classification Search
USPC ..... 623/17.11–17.16; 606/246–253; 128/897, 128/898
See application file for complete search history.

(56) References Cited

U.S. PATENT DOCUMENTS

| | | | | |
|---|---|---|---|---|
| 6,626,944 B1 * | 9/2003 | Taylor | ......................... | 623/17.16 |
| 6,761,720 B1 * | 7/2004 | Senegas | ......................... | 606/249 |
| 7,087,083 B2 * | 8/2006 | Pasquet et al. | ............. | 623/17.11 |

FOREIGN PATENT DOCUMENTS

| | | | |
|---|---|---|---|
| FR | 2 799 640 | | 4/2001 |
| JP | 11-89854 | | 4/1999 |
| JP | 2000-70277 | | 3/2000 |
| JP | 2003-79649 | | 3/2003 |
| WO | WO 01/28442 | * | 4/2001 |
| WO | WO 02/071960 | * | 9/2002 |
| WO | 2004/084743 A1 | | 10/2004 |

\* cited by examiner

*Primary Examiner* — Michael T Schaper
(74) *Attorney, Agent, or Firm* — Seager, Tufte & Wickhem, LLC

(57) ABSTRACT

Intervertebral spacer to be placed between two adjacent, upper and lower cervical vertebrae, the spacer comprising a spacer body and retention member for retaining the spacer body in position against said vertebrae. The retention member includes a strap and fastener member that are removable and self-blocking, enabling the ends of the strap to be secured to the spacer body. The spacer body including: a spacer part having two opposite ends, a portion of the first end configured to be inserted between the vertebrae; and top and bottom flanges connected via their bases to the second end of the spacer part and extending on either side thereof, each flange presenting an anterior face facing towards the spacer part and configured to bear against the posterior portion of the lamina of the upper or lower vertebra, respectively.

16 Claims, 4 Drawing Sheets

INTERVERTEBRAL SPACER FOR CERVICAL VERTEBRAE

BACKGROUND OF THE INVENTION

The present invention relates to an intervertebral spacer for inserting between two adjacent cervical vertebrae, and to a set of intervertebral spacers comprising two intervertebral spacers of the above-specified type.

The human spine is made up of twenty-four true vertebrae placed one above the other and connected together by pieces of fibrocartilage known as intervertebral disks. These vertebrae constitute three groups: seven cervical vertebrae, twelve dorsal vertebrae, and five lumbar vertebrae. The vertebrae are of different shapes in the three regions (cervical dorsal, and lumbar) of the spine, but they all retain certain general characteristics. Every vertebra comprises:

an enlarged anterior portion known as the vertebral body;

a bony arch that is concave on the anterior side, generally referred to as the posterior arch or neural arch, and that co-operates with the posterior face of the vertebral body to circumscribe an orifice (known as the vertebral foramen) through which the spinal cord passes, said arch being formed on either side by front pedicles and by rear vertebral laminae; and a middle posterior projection known as the spinous process.

During the life of an individual, it can happen that an intervertebral disk becomes damaged, for various reasons. Under such circumstances, the stresses that act on said disk as a result of relative displacements between the two vertebrae on either side of the disk give rise to pain. Thus, in order to relieve such pain, attempts are made to hold the two vertebrae stationary relative to each other.

Numerous vertebral spacers are already known for placing between two adjacent dorsal or lumbar vertebrae. Such spacers generally present two longitudinally-extending notches formed respectively in their top and bottom faces, each serving to receive the spinous process of one of the two vertebrae. An example of a spacer of that type can be found in the French patent application made public under publication No. FR 2 799 640.

Although that type of prior art spacer is well adapted to the dorsal and lumbar regions, it is nevertheless impossible to use it with cervical vertebrae, in part for the following reasons.

Firstly, the spine in the cervical region is convex in the anterior direction, known as cervical lordosis, which means that the spinous processes of the vertebrae are moved towards one another. As a result, these processes are so close together (some processes touch one another) that it is not possible to install a spacer between them.

Secondly, whereas in the dorsal or lumbar region the relative movements between two adjacent vertebrae consist mainly in the vertebrae moving apart or towards each other, where these movements are caused respectively by the spine flexing or extending, in the cervical region, the movements involved are more complex. Thus, there are movements of one vertebra turning relative to another caused by twisting the spine, or movements caused by the spine being flexed laterally (i.e. the spine moves laterally away from the sagittal plane), which can be resolved into a rotation and an asymmetrical movement apart between one vertebra and another, and these movements are much more marked in the cervical region than in the dorsal or lumbar regions.

SUMMARY OF THE INVENTION

An object of the invention is thus to provide an intervertebral spacer for putting into place between two adjacent upper and lower cervical vertebrae in order to limit the relative displacement of said vertebrae.

The seven cervical vertebrae are usually numbered starting from the top of the spine, being referred to as C1 to C7. The vertebra C1 is also known as the atlas and the vertebra C2 as the axis. The altlanto-axial intervertebral region (i.e. situated between the vertebrae C1 and C2) is anatomically very different from the lower intervertebral regions, in particular because of the shape of the vertebra C1.

The spacer of the invention is intended more particularly for putting into place between two adjacent cervical vertebrae other than the atlas and the axis, i.e. between two adjacent vertebrae selected from C2 to C7.

In the most general embodiment, the spacer of the invention comprises a spacer body and retention means for retaining the spacer body in position against said adjacent, upper and lower cervical vertebrae, said spacer body comprising:

a spacer part having two opposite ends, a portion of the first end being suitable for being inserted between the top end wall of the lamina of the lower cervical vertebra and the bottom end wall of the lamina of the upper cervical vertebra;

top and bottom flanges having their bases connected to the second end of the spacer part and extending from either thereof, each flange presenting an anterior face facing towards the spacer part and a posterior face, the anterior faces of the top and bottom flanges being suitable for coming to bear against the posterior portions of the laminae of the upper and lower vertebrae, respectively.

The particular shape of this spacer enables it to adapt to the morphology of the cervical region in order to perform its function. In particular, the spacer part holds the laminae of the upper and lower cervical vertebrae at a distance apart from each other, thereby enabling the intervertebral disk to be relieved of certain compression stresses, and in particular serving to avoid any "pinching" associated with extension of the spine.

Furthermore, by bearing against the laminae of the vertebrae, the top and bottom flanges guarantee that the spacer body has a position that is stable relative thereto.

Said retention means for retaining the spacer body in position against said vertebrae comprise a strap having two ends and self-blocking fastener means enabling at least one of the ends of the strap to be secured to the spacer body, said strap being for tightening around the laminae of the upper and lower vertebrae.

The retention means thus clamp together the spacer body and the vertebral laminae, thus enabling the spacer part that is engaged between said laminae to be kept in place and prevent it from escaping. These means thus guarantee that the spacer is kept in position once it has been implanted, regardless of the movements performed by the patient on whom the operation has been performed.

In addition, said retention means prevent the vertebrae from moving apart from one another, thereby protecting the intervertebral disk from any stress, in particular when flexing the spine.

In practice, in order to limit relative displacement between two adjacent vertebrae, it is necessary to make use of two intervertebral spacers of the type described above. That is why the invention also provides a set of intervertebral spacers, characterized in that it comprises first and second intervertebral spacers of the above-specified type, the first spacer being for placing between the laminae of the upper and lower cervical vertebrae situated on one side of the spinous processes of said vertebrae, and the second spacer being for placing between the laminae of the upper and lower cervical vertebrae situated on the other side of said spinous processes.

This combination of two spacers serves to prevent any relative movement between the two vertebrae in question: movement apart, movement towards each other, or movement in rotation, and this applies regardless of the general movement of the spine: extension, flexion, twisting, or lateral bending.

BRIEF DESCRIPTION OF THE DRAWINGS

The various characteristics and main advantages of the invention can be better understood on reading about particular embodiments of intervertebral spacers given by way of example and shown in the following figures:

FIG. 3A is a section view of the FIG. 3 spacer once it has been put into place between two vertebrae;

DETAILED DESCRIPTION OF THE PREFERRED EMBODIMENT(S)

Figure 1:
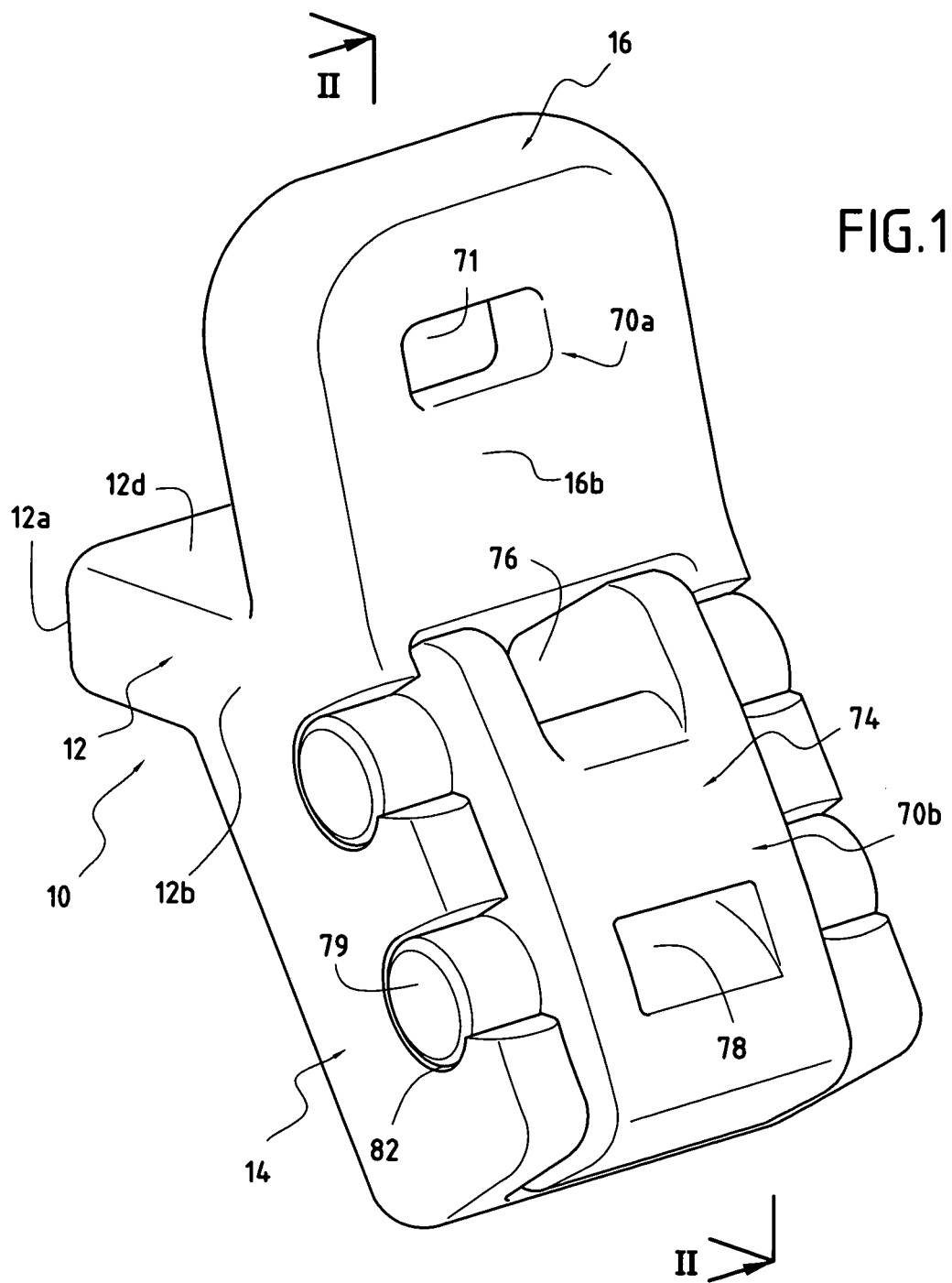
FIG. 1 is an outside perspective view of a first type of spacer of the invention.

In a first embodiment of the invention, and with reference to FIGS. 1, 2, and 2A, the spacer comprises a spacer body 10, itself comprising a spacer part 12 having a distal first end 12a and a proximal second end 12b from which there extend above and below the part 12, a top flange 16 and a bottom flange 14. Each flange 14 and 16 presents a respective anterior face 14a, 16a facing in the same direction as the spacer part 12, and a posterior face 14b, 16b opposite from the corresponding anterior face.

The spacer body 10 is symmetrical about its midplane II-II shown in FIG. 1, which plane is parallel to the direction in which distance is measured between the distal end 12a and the proximal end 12b of the spacer part 12.

The spacer part 12 of the spacer body 10 is for insertion between two cervical vertebrae, an upper vertebra V2 and a lower vertebra V1. In the example shown, the part 12 presents opposite top and bottom faces 12d and 12c that are substantially parallel to each other. The top face 12d is for coming into contact with the bottom end wall of the lamina of the upper vertebra V2 while the bottom face 12c is for coming into contact with the top end wall of the lamina of the lower vertebra V1.

In order to keep the vertebrae V1 and V2 at a certain distance apart, the key dimension is naturally the thickness E between the faces 12c and 12d of the spacer part 12. Advantageously, this thickness E is selected to lie in the range 2 millimeters (mm) to 8 mm. It has been found that such a thickness is effective in relieving the intervertebral disk situated between the vertebrae V1 and V2.

Another characteristic of the spacer part 12 is the distance D1 between its distal first end 12a and the base of the bottom flange 14. This distance D1 determines the depth to which the part 12 penetrates between the vertebrae V1 and V2. Thus the distance D1 must be long enough for the spacer to remain in position between the vertebrae V1 and V2, regardless of their movements. The distance D1 must also be short enough to ensure that the end 12a does not advance too far into the vertebral foramen. It is appropriate to avoid excessive contact between said end 12a and the spinal cord since that can cause the patient pain. Nevertheless, it should be observed that in the cervical region the spinal cord is protected by a ligament known as the yellow ligament, such that light contact between said ligament and the end 12a can be accepted. In practice, the distance D1 can be selected to lie in the range 2 mm to 6 mm.

The distance D2 between the first end 12a of the spacer part 12 and the base of the top flange is defined as a distance D2, and the distance d is defined as the difference between D2 and D1 (d=D2−D1).

Advantageously, the distance D2 is selected so that d lies in a range that enables the spacer body to adapt to the natural offset that exists between the cervical vertebrae. Because of cervical lordosis, the top end wall of the lamina of the lower vertebra is set back relative to the bottom end wall of the lamina of the adjacent upper vertebra. Thus, the distance d=D2−D1 advantageously lies in the range 0 to 5 mm.

In addition, another consequence of cervical lordosis is that the laminae of the cervical vertebrae are inclined relative to one another. Advantageously, in order to accommodate this inclination, the anterior face 16a of the top flange 16 forms an angle (β−α) with the anterior face 14a of the bottom flange 14 that lies in the range 0 to 60°. In the example shown, the angle (β−α) can be measured without difficulty since the anterior faces 16a and 14a are substantially plane. When that is not the case, the angle (β−α) should be measured between the midplanes of the faces 16a and 14a.

The intervertebral spacer of the invention also comprises retention means for retaining the spacer body 10 in position between the vertebrae V1 and V2. A first type of retention means is shown in FIGS. 1 to 3.

These retention means comprise a strap 60 having two ends 60a and 60b, and fastener means 70 that enable the ends 60a and 60b to be secured to the spacer body 10. The fastener means 70 comprise first fastener means 70a situated on one of the flanges of the spacer body 10, in this case the top flange 16, and self-blocking, second fastener means 70b situated on the other flange of the spacer body 10, in this case the bottom flange 14. The first and second fastener means 70a and 70b serve respectively to secure the first and second ends 60a and 60b of the strap 60 to the spacer body 10.

The first fastener means 70a comprise a slot 71 formed in the top flange 16 through which an end portion 60a of the strap is passed prior to the end 60a being stitched (or secured by any other means) to the strap itself so as to form a loop surrounding the portion of the top flange 16 that is situated above the slot 71.

The second end of the strap 60b is passed and then pulled through the second fastener means 70b to tighten the strap 60 around the laminae of the upper and lower vertebrae V2 and V1. The second fastener means are made in such a manner as to give rise to friction forces that oppose loosening of said strap. That is why the fastener means are said to be self-blocking. In the example shown in FIGS. 1, 2, and 2A, the second fastener means 70b are removable from the spacer body 10 and are suitable for being fitted onto the posterior face 14b of the bottom flange 14.

The second fastener means 70b present an anterior face 72 and a posterior face 74 (opposite from the face 72), and they are pierced by first and second slots 76 and 78 that open out into said faces 72 and 74. Although these slots are not necessarily strictly parallel to each other, they are both inclined in the same direction relative to the faces 72 and 74.

The second end 60b of the strap 60 is passed through the slots 76 and 78 as follows: the strap is inserted into the first slot 76 from beside the anterior face 72, and leaves it beside the posterior face, it is then inserted into the second slot 78 beside the posterior face 74 and leaves it beside the anterior face 72. Thus, a portion 60c of the strap situated upstream from the first slot 76 overlaps a portion 60d of the strap situated downstream from the second slot 78.

A housing 80 is formed in the posterior face 14b of the flange 14 of the spacer body 10 for receiving the second fastener means 70b. Openings 82 are formed in the side walls 81 of the housing 80 and are suitable for co-operating with studs 79 present on the side wall of the second fastener means 70b by snap-fastening. Thus, the second fastener means 70b can be fitted onto the spacer body 10.

Once the second fastener means have been fitted onto the spacer body 10, the strap portions 60c and 60d that overlap are pressed against each other so that significant friction forces exist therebetween. Furthermore, the second slot 78 co-operates with the posterior face 82 of the fastener means 70b to form an acute angle such that the edge 77 situated at the outlet (in the threading direction of the strap 60) of the second slot 78 is sharp. The friction forces between this edge 77 and the strap 60 are also significant. Once the strap 60 has been tightened around the laminae of the vertebrae V1 and V2, the above-mentioned friction forces oppose any loosening of the strap.

FIGS. 3, 3A, 4, and 5 show a second embodiment of a spacer of the invention.

The spacer comprises a spacer body 10 substantially identical to that described above. That is why those portions of the spacer body in FIGS. 3 to 5 that are analogous to portions of the spacer body in FIGS. 1 and 2 are given the same reference numerals. The major difference between the two spacer bodies lies in the fact that in the second embodiment the posterior faces 16b and 14b of the top and bottom flanges 16 and 14 are coplanar.

In contrast, in this second embodiment, the spacer has retention means for retaining the spacer body 10 in position against the vertebrae V1 and V2 that are different from the retention means described above.

The retention means comprise a strap 160 presenting two ends 160a and 160b, and self-blocking fastener means 170 enabling the two ends 160a and 160b to be secured to the spacer body 10. These self-blocking fastener means 170 extend over the posterior faces 16b and 14b of the top and bottom flanges 16 and 14. This disposition is made easier in the embodiment shown by the fact that the two posterior faces 16b and 14b are coplanar. Nevertheless, the means 170 could be situated on one only of the posterior faces 16b and 14b.

The self-blocking fastener means 170 are removable from the spacer body 10 and are provided on their side walls with studs 179 (two studs per side wall) suitable for connecting by snap-fastening in openings 182 formed in the side walls 181 of the posterior portion of the spacer body 10. These side walls 181 co-operate with the posterior faces 14b and 16b of the flanges 14 and 16 to define a housing 180 suitable for receiving said self-blocking fastener means 170.

The fastener means 170 present an anterior face 172 and a posterior face 174 and they are pierced by three successive through slots 171, 173, and 175 that open out into both of the faces 172 and 174. The first and third slots 171 and 175 are inclined towards each other, while the central, second slot 173 is a V-shaped slot. These fastener means 170 presents a plane of symmetry corresponding to the midplane of the V-shaped slot 173. This plane of symmetry subdivides the fastener means 170 into two half-assemblies 170' and 170", the slot 173 itself being subdivided into two half-slots 173' and 173".

Figure 2A:
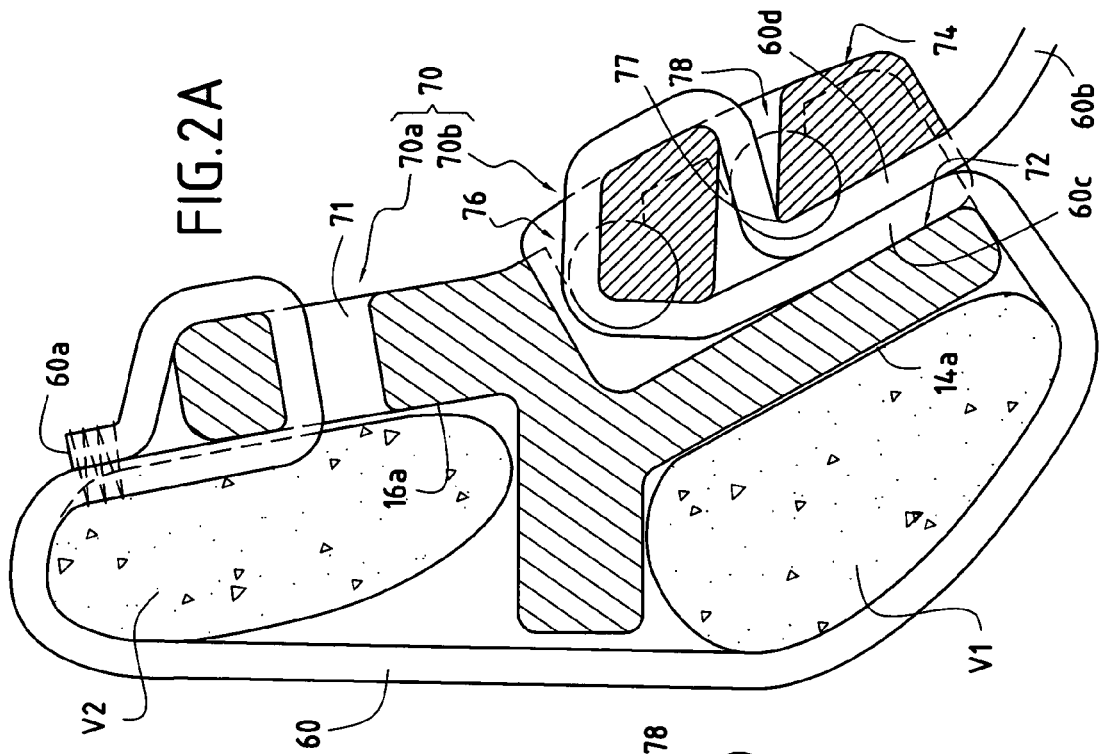
FIG. 2A is a section view of the spacer of FIGS. 1 and 2 once it has been put into place between the laminae of two adjacent cervical vertebrae.
Figure 2:
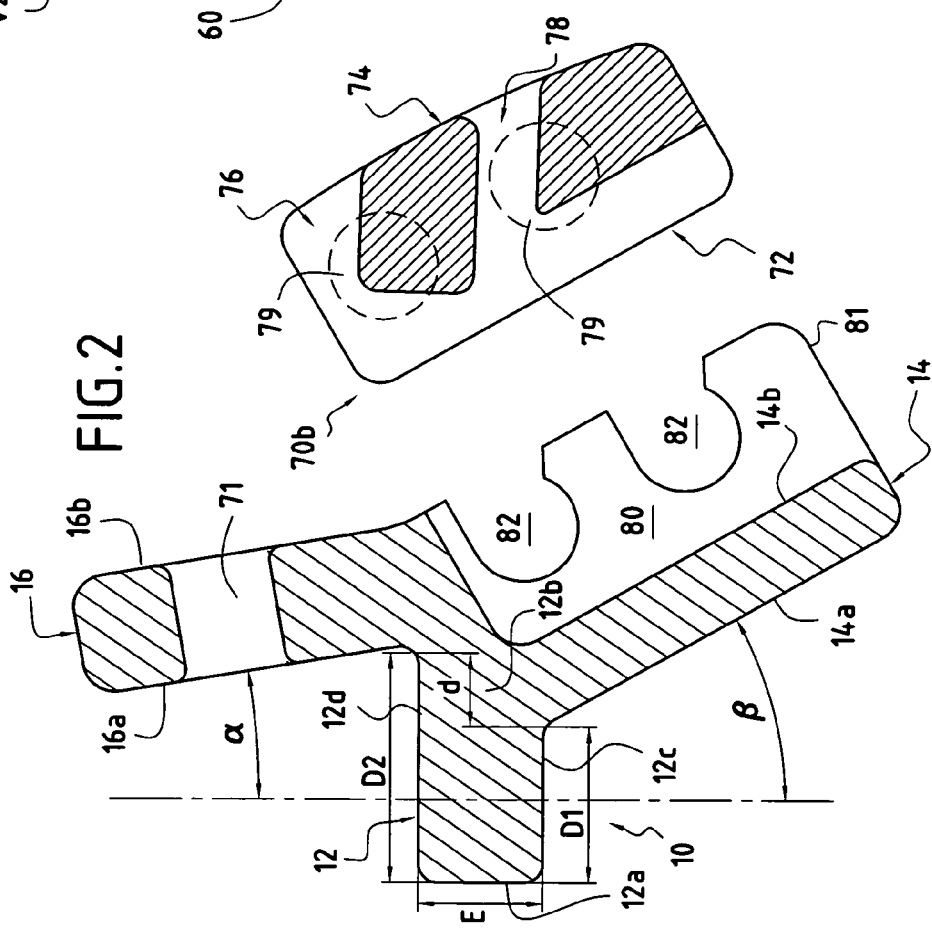
FIG. 2 is an exploded view in section on plane II-II of the spacer shown in FIG. 1.
Figure 3:
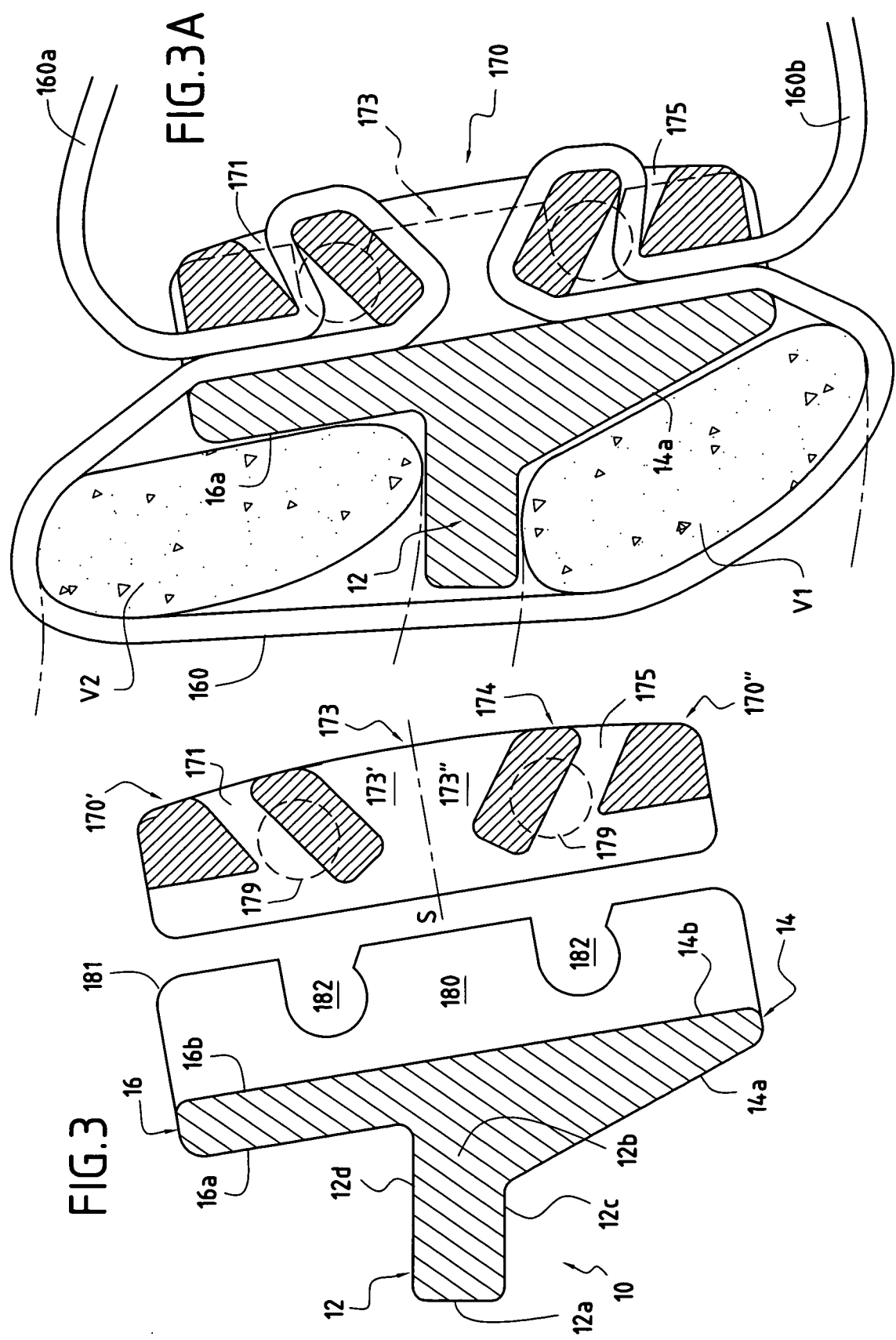
FIG. 3 is an exploded section view of a second type of spacer of the invention.

The structure of either half-assembly 170' or 170" is analogous to the structure of the fastener means 70b described and shown with reference to FIGS. 1, 2, and 2A. In particular, the two slots 171 and 173' or 175 and 173" are equivalent respectively to the first and second slots 78 and 76 of the means 70b. Thus, the strap ends 160a and 160b are passed respectively through the slot systems 171 and 173', and 175 and 173" in the same manner as the end 60b is passed through the slot system 76 and 78, such that friction forces serve to oppose loosening of the strap 160 once it has been tightened around the vertebrae V1 and V2.

Figure 4:
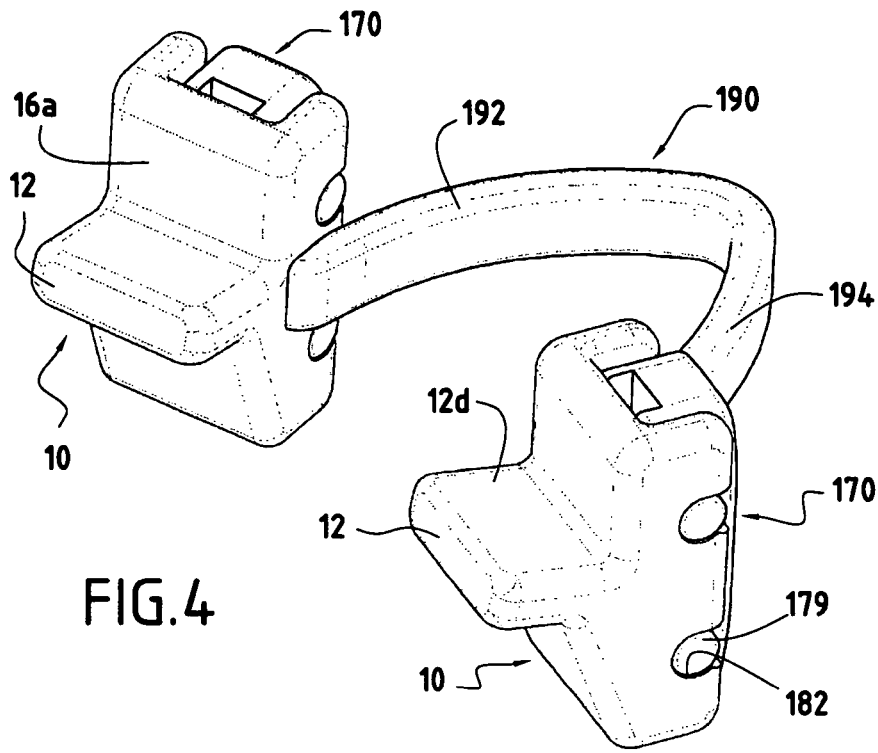
FIG. 4 is an external perspective view of a set of two spacers of the type shown in FIGS. 3 and 3A.
Figure 5:
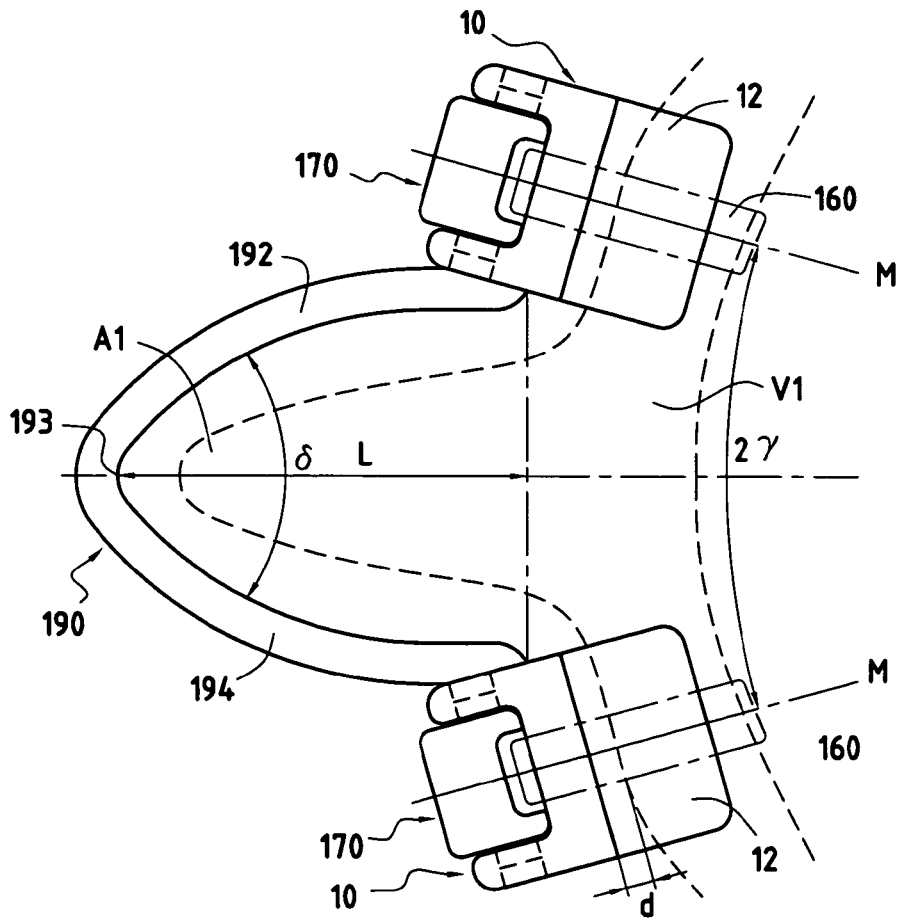
FIG. 5 is a plan view of the FIG. 4 assembly once it has been put into place between two vertebrae.

With reference to FIGS. 4 and 5, there follows a description of an example of a set of intervertebral spacers, comprising two spacers of the type shown in FIGS. 3 and 3A, together with a connection element 190 that presents some degree of rigidity and is of a shape that is selected to that the element 190 goes round the spinous processes A1 of the adjacent lower and upper vertebrae V1 and V2.

In the example, said connection element 190 is generally V-shaped presenting two curved limbs 192, 194 that are spaced apart from each other, with their free ends secured to the first and second spacers 170. The length of the limbs 192, 194, their curvature, and their spacing angle δ are selected so that the junction element 190 goes round the processes A1 of the vertebrae V1, V2, and the distance L between the free ends of the branches 192, 194 and the junction point 193 between said branches is advantageously selected to lie in the range 10 mm to 40 mm, with the spacing angle δ between said branches lying in the range 10° to 60°.

The shape of the connection element 190 and the way in which it is secured to the spacers 170 are such that the midplanes M of the spacer parts 12 of the spacers 170, said planes M being oriented in the thickness direction of the spacer part 12, define between them a rectilinear dihedral angle 2γ (it should be observed that the plane M corresponds to the plane II-II of FIG. 1). The angle 2γ is selected in such a manner that when one of the spacers 170 is installed between the laminae of the vertebrae V1 and V2 on one side of the spinous processes A1 of said vertebrae, the other spacer 170 is positioned (or at least attempts to position itself) in the proper location between the laminae of the vertebrae V1 and V2 situated on the other side of the processes A1. Advantageously, the 2γ lies in the range 0 to 60°.

This set of spacers thus makes the work of the surgeon easier while putting the spacers 70 into place, firstly because the surgeon needs to handle only one assembly instead of two separate spacers, and secondly because positioning of the spacers 170 guides the positioning of the other spacer.

The structure of the spacers and of the set of spacers of the invention is described above, and there follows a description of a method of how the spacers are put into place between two adjacent cervical vertebrae V2 and V1.

Such a method comprises the following steps:

providing an access path to the posterior portion of the spine, in the vicinity of said cervical vertebrae V1 and V2;

installing the spacer body of a first spacer of the type described above between the laminae of said cervical vertebrae situated on one side of the spinous processes A2, A1 of said vertebrae;

securing the spacer body on said first spacer to said vertebrae V2, V1 and retaining it in position against the vertebrae using the retention means of the type described above;

installing the spacer body of a second spacer, identical to the first, between the laminae of said cervical vertebrae V2 and V1, situated on the other side of the spinous processes A1 of said vertebrae; and securing the spacer body of said second spacer to said vertebrae V2, V1 and retaining it in position against the vertebrae with the help of retention means of the type described above.

The above-described first and second spacers may be independent from each other, or they may belong to a set of spacers of the type described above.

The invention claimed is:

1. An intervertebral spacer to be placed between two adjacent, upper and lower, cervical vertebrae, the spacer comprising:
   a spacer body having a spacer part, a top flange and a bottom flange each extending from a base of the spacer body in diverging directions such that the spacer part extends from the base to a first end surface of the spacer part in a first direction, the top flange extends from the base in a second direction different from the first direction, and the bottom flange extends from the base in a third direction different from the first and second directions;
   the spacer part having a superior face and an inferior face each extending from the base to the first end surface, the superior face and the inferior face being parallel to each other from the base to the first end surface;
   the top flange having an anterior face and a posterior face;
   the bottom flange having an anterior face and a posterior face;
   wherein the anterior face of the top flange intersects the superior face of the spacer part at an angle, and the anterior face of the bottom flange intersects the inferior face of the spacer part at an angle;
   wherein a portion of the first end surface of the spacer part is suitable for being inserted between a top end wall of a lamina of the lower cervical vertebra and a bottom end wall of a lamina of the upper cervical vertebra while the anterior faces of the top and bottom flanges come to bear against the posterior portions of the laminae of the upper and lower vertebra, respectively; and
   a retention means for retaining the spacer body in position comprising a strap having a first end and a second end and self-blocking fastener means enabling at least one of the ends of the strap to be secured to the spacer body, the strap having a length for tightening around the laminae of the upper and lower vertebrae.

2. An intervertebral spacer according to claim 1, wherein the angle between the anterior face of the top flange and the superior face of the spacer part is different from the angle between the anterior face of the bottom flange and the inferior face of the spacer part.

3. An intervertebral spacer according to claim 1, wherein the superior face of the spacer part has a length extending from the first end surface of the spacer part to the anterior face of the top flange, and the inferior face of the spacer part has a length extending from the first end surface of the spacer part to the anterior face of the bottom flange, the length of the superior face of the spacer part being greater than the length of the inferior face of the spacer part.

4. An intervertebral spacer to be placed between two adjacent, upper and lower, cervical vertebrae, the spacer comprising:
   a spacer body and retention means for retaining the spacer body in position against said vertebrae,
   said spacer body comprising:
      a spacer part having opposite first and second ends defining a direction from the second end to the first end, and upper and lower surfaces extending between the first and second ends, a portion of the first end being suitable for being inserted between a top end wall of a lamina of the lower cervical vertebra and a bottom end wall of a lamina of the upper cervical vertebra;
      top and bottom flanges having respective bases connected to the second end of the spacer part, the top flange diverging from the second end of the spacer part in a first direction and the bottom flange diverging from the second end of the spacer part in a second direction different from the first direction, wherein the spacer part extends away from each flange to a first end surface of the spacer part, each flange presenting an anterior face generally facing the same direction as the first end surface of the spacer part, and a posterior face, the anterior faces of the top and bottom flanges being suitable for coming to bear against posterior portions of the laminae of the upper and lower vertebra, respectively;
      wherein the upper surface defines a first distance extending along the upper surface from an intersection of the upper surface with the first end surface to an intersection of the upper surface with the anterior face of the top flange, and the lower surface defines a second distance extending along the lower surface from an intersection of the lower surface with the first end surface to an intersection of the lower surface with the anterior face of the bottom flange, the first distance being greater than the second distance;
   wherein said retention means for retaining the spacer body in position comprises a strap having a first end and a second end and self-blocking fastener means enabling at least one of the ends of the strap to be secured to the spacer body, said strap having a length for tightening around the laminae of the upper and lower vertebrae.

5. An intervertebral spacer according to claim 4, wherein said retention means for retaining the spacer body in position comprises first fastener means situated on one of the flanges of the spacer body for securing the first end of said strap to the spacer body, and self-blocking second fastener means situated on the other flange of the spacer body, with the second end of the strap being passed therethrough and then pulled in order to tighten the strap around the laminae of the upper and lower vertebrae, the second fastener means being made in such a manner as to give rise to friction forces that oppose loosening of said strap.

6. An intervertebral spacer according to claim 4, wherein said self-blocking fastener means are situated on the posterior face of the top flange or of the bottom flange, the first and second ends of the strap being passed through said fastener means and then pulled in order to tighten the strap around the laminae of the upper and lower vertebrae, said self-blocking fastener means being made in such a manner as to give rise to friction forces that oppose loosening of said strap.

7. An intervertebral spacer according to claim 6, wherein the posterior faces of the top and bottom flanges are coplanar.

8. An intervertebral spacer according to claim 4, wherein said self-blocking fastener means is removable from the spacer body and is fitted on the posterior face of the top flange or of the bottom flange.

9. An intervertebral spacer according to claim 4, wherein said self-blocking fastener means are situated on the posterior faces of the top flange and of the bottom flange, the first and second ends of the strap being passed through said fastener means and then pulled in order to tighten the strap around the laminae of the upper and lower vertebrae, said self-blocking fastener means being made in such a manner as to give rise to friction forces that oppose loosening of said strap.

10. An intervertebral spacer according to claim 9, wherein the posterior faces of the top and bottom flanges are coplanar.

11. An intervertebral spacer according to claim 4, wherein said self-blocking fastener means is removable from the spacer body and is fitted on the posterior face of the top flange and of the bottom flange.

12. A set of intervertebral spacers, comprising an intervertebral spacer according to claim 4, wherein the intervertebral spacer is a first intervertebral spacer, the set further comprising a second intervertebral spacer identical to the first intervertebral spacer, the first spacer to be placed between the laminae of the upper and lower cervical vertebrae situated on one side of a spinous processes of said vertebrae, and the second spacer being for placing between the laminae of the upper and lower cervical vertebrae situated on the other side of said spinous processes.

13. A set of intervertebral spacers according to claim 12, further comprising a connection element interconnecting the spacers.

14. A set of intervertebral spacers according to claim 13, wherein the shape of said connection element is selected in such a manner that said element goes around the spinous processes of said vertebrae.

15. A set of intervertebral spacers according to claim 14, wherein said connection element is generally V-shaped and includes two curved limbs that are spaced apart from each other, having free ends that are secured to the first and second spacers, the length of the limbs, their curvature, and their spacing angle being selected in such a manner that the connection element goes around the spinous processes of said vertebrae.

16. A set of intervertebral spacers according to claim 15, wherein the distance between the free ends of the limbs and a junction point between said limbs lies in the range 10 mm to 40 mm, and said spacing angle between said limbs lies in the range 10° to 60°.

* * * * *